(12) United States Patent
Vetter et al.

(10) Patent No.: US 7,953,470 B2
(45) Date of Patent: May 31, 2011

(54) METHOD, DEVICE AND NAVIGATION AID FOR NAVIGATION DURING MEDICAL INTERVENTIONS

(75) Inventors: Marcus Vetter, Edingen (DE); Peter Hassenpflug, Wartenberg (DE); Gerald Glombitza, Dossenheim (DE); Ivo Wolf, Wissenbach (DE); Hans-Peter Meinzer, Heidelberg (DE)

(73) Assignee: Deutsches Krebsforschungszentrum Stiftung des öffentlichen Rechts, Heidelberg (DE)

( * ) Notice: Subject to any disclaimer, the term of this patent is extended or adjusted under 35 U.S.C. 154(b) by 1125 days.

(21) Appl. No.: 10/399,828

(22) PCT Filed: Oct. 23, 2001

(86) PCT No.: PCT/DE01/03971
§ 371 (c)(1),
(2), (4) Date: Aug. 29, 2003

(87) PCT Pub. No.: WO02/34152
PCT Pub. Date: May 2, 2002

(65) Prior Publication Data
US 2004/0059216 A1 Mar. 25, 2004

(30) Foreign Application Priority Data

Oct. 23, 2000 (DE) .................................. 100 52 516
Oct. 23, 2000 (DE) .................................. 100 52 519

(51) Int. Cl.
*A61B 5/05* (2006.01)
(52) U.S. Cl. ........................................ 600/424; 600/434
(58) Field of Classification Search .................. 600/414, 600/407, 461, 417, 437–439, 424, 434; 128/899, 128/915, 916, 920; 606/130
See application file for complete search history.

(56) References Cited

U.S. PATENT DOCUMENTS

| | | | | |
|---|---|---|---|---|
| 5,662,111 A | * | 9/1997 | Cosman | 600/417 |
| 5,853,366 A | * | 12/1998 | Dowlatshahi | 600/434 |
| 5,868,673 A | * | 2/1999 | Vesely | 600/407 |
| 6,175,760 B1 | * | 1/2001 | Baskin et al. | 600/436 |
| 6,499,488 B1 | * | 12/2002 | Hunter et al. | 128/899 |

FOREIGN PATENT DOCUMENTS
WO WO9838908 9/1998
* cited by examiner

*Primary Examiner* — Long V. Le
*Assistant Examiner* — Sanjay Cattungal
(74) *Attorney, Agent, or Firm* — Collard & Roe, P.C.

(57) ABSTRACT

The invention relates to one or several navigation aids whose position can be used to maintain the recorded state of at least one partial structure of a non-bone structure. The navigation aid(s) is/are inserted into the non-bone structure.

18 Claims, 3 Drawing Sheets

METHOD, DEVICE AND NAVIGATION AID FOR NAVIGATION DURING MEDICAL INTERVENTIONS

CROSS REFERENCE TO RELATED APPLICATIONS

Applicants claim priority under 35 U.S.C. §119 of German Applications Nos. 100 52 519.9, filed on Oct. 23, 2000 and 100 52 516.4, filed on Oct. 23, 2000. Applicants also claim priority under 35 U.S.C. §365 of PCT/DE01/03971 filed on Oct. 23, 2001. The international application under PCT article 21(2) was not published in English.

The invention relates to a method, a device and a navigation aid for navigation during medical interventions on non-osseous structures. In doing so, the invention relates in particular to the field of medical interventions on soft tissue structures of a body.

Previously, during such interventions a therapist was substantially dependent on his sense of feel and sight. This has the result in particular that safety margins from vital regions of the body often cannot be maintained. In addition, when proceeding in such a manner, orientation is not clear to other persons. This becomes extremely difficult in particular to the extent that such soft tissue structures generally change their position during the intervention, so that vital structures may be located at a different position than at the beginning of the intervention. The shape of the organs to be operated on is also changed by the intervention, which likewise leads to deviations.

Precise navigation is absolutely necessary in particular for maintaining safety margins, in particular also in the vicinity of vital structures.

The present invention is concerned with permitting more objective and precise navigation during medical interventions on non-osseous structures.

As a solution achieving this, the invention proposes on the one hand registration of the non-osseous structure with its preoperative data, defined fixing of at least one navigation aid on or in the non-osseous structure and determination of the position of at least one substructure of the non-osseous structure on the basis of the position of the navigation aid.

Such a navigation aid makes it possible to define a locally exact system of coordinates which is invariant over the course of the operation that permits visual representation of the operating surgeon's instruments or the like in relation to important structures in the organ operated on. This applies all the more precisely the closer the navigation aid is fixed in the vicinity of a planned cut or a site of interest. In particular if the navigation aid is fixed in the structure, it can also be used for navigation in the depth of an organ or soft tissue. To this extent, the procedure according to the invention makes it possible for the first time in a non-osseous structure, such as in particular an organ or soft tissue, for exact details concerning the movement or changing of the non-osseous structure, even in terms of depth, to be conveyed to an operating surgeon even if the surgeon cannot see the actual operating site.

The positional determination preferably takes place at least cumulatively in a data-processing system, whereby the configuration of the navigation method according to the invention is simplified considerably. For this purpose, an image data record of the non-osseous structure, as can be obtained for example by means of MR or CT, can be stored in advance, for example as part of planning for the operation. The position of the substructure, which is generally likewise contained in this image data record, is preferably determined on the basis of this image data record. To this end, the organ to be operated on, including its important substructures, such as for example vessels and tumors, are segmented—that is represented in its spatial position from an image data record in object form—, for example in the preoperative image data record, and the position of resection surfaces and navigation aids for the navigation determined in the preoperative data.

At the beginning of the intervention, the position of the navigation aid anchored at the beginning on or in the non-osseous structure is preferably first determined with respect to the non-osseous structure in the image data record, or, after previous planning, the navigation aid is introduced in an already navigated manner to the previously determined location and anchored. For this purpose, the non-osseous structure is preferably itself immobilized or fixed, whereby this positional determination and anchoring of the navigation aid is considerably facilitated. After the attachment or introduction of the navigation aid or after the positional determination of the navigation aid, the immobilization or fixing of the non-osseous structure can be discontinued, so that the immobilization or fixing of the non-osseous structure takes place for as short a time as possible, in order to put as little strain as possible on the organism.

To this extent, on the one hand the non-osseous structure can be registered before introduction of the navigation aid, that is matched with regard to its preoperative and intraoperative data, so that the navigation aid can be attached or introduced in a correspondingly navigated manner. In this way it can be ensured that the navigation aid is set as optimally as possible in a way corresponding to previous planning for the operation.

On the other hand, it is also possible to perform the registration of the non-osseous structure after introduction of the navigation aid, it then being possible in particular to perform a registration of the navigation aid at the same time. This procedure has the advantage that the overall operating time can be shortened to the effect that only a registration step need be performed during the intervention.

In the present connection, a distinction has to be made on the one hand between preoperative and intraoperative data, procedures or measures. "Preoperative" is used here to refer to data, procedures or measures which are obtained or carried out prior to an operation or treatment. "Intraoperative" is used to refer to data, procedures or measures which are acquired or carried out interventionally, i.e. during the actual intervention, on the patient. Interventional interventions are preferably open surgical interventions and minimally invasive forms of diagnosis and therapy, such as for example LITT (Laser-Induced Thermotherapy), RFA (Radio-Frequency Ablation) and cryotherapy.

On the other hand, in the case of interventional data, procedures and measures, a distinction must be made between "premutative" data, procedures and measures, "intramutative" data, procedures and measures and "postmutative" data, procedures and measures, the "premutative" data, procedures and measures being obtained or carried out before irreversible procedures or measures, such as for example a resection, are carried out, the intramutative data, procedures and measures being obtained or carried out during this time and the "postmutative" data, procedures and measures being obtained or carried out after irreversible procedures or measures have been carried out.

To this extent, registration can establish a relationship both between preoperative and premutative data and between preoperative and intra- or postmutative data. It proves to be advantageous for the precision of the method according to the invention to perform registration initially between preoperative and premutative data. Following this, the course of an operation, in which the non-osseous structure changes its position, form and shape considerably, for example as the result of a resection, can then be correspondingly traced by matching with postmutative data. When doing so, it has been found that frequent matching during the operation considerably increases the accuracy with which the sequence of movements is traced. In addition, it has been found that matching of the intraoperative data with one another, that is matching between pre- and postmutative data, or matching between postmutative data recorded in different, preferably successive, stages of the operation, can take place much more quickly than is the case with matching between preoperative and postmutative data. In this way, real-time navigation can consequently be realized with technically simpler means.

For positional determination, a transformation can then be determined on the basis of the position of the navigation aid at the beginning of the intervention (in particular premutatively) and the position of the navigation aid during the intervention (in particular intramutatively or postmutatively) and this transformation applied to the image data record of the substructure or of the entire non-osseous structure for the positional determination of the substructure or else of the entire non-osseous structure. It goes without saying here that this transformation will be much more accurate in the vicinity of the navigation aid than is the case with substructures which are further away. Such a transformation consequently permits an assignment between intraoperative image data and preoperative image data. Since such a transformation can be chosen invertibly, given a suitable choice of the associated systems of coordinates, which should respectively cover all the necessary spatial dimensions, an assignment of the preoperative image data to the intraoperative image data is then also readily possible.

By conducting the method in such a way, a geometrical assignment of image data recorded prior to the intervention to the current position of the partial region is possible, so that safety margins can be maintained even under adverse visual and palpatory conditions. By representing the current position and instrument position in the pre- and intraoperative image data, it is additionally possible for third parties to obtain an objective picture of the navigation.

In this connection, it goes without saying that the transformation does not necessarily have to be determined from the actual image data but that it can also take place on the basis of other data corresponding to the image data, such as for example on the basis of measured data. To this extent, the term "image data" in the present connection refers to any data record which permits a characterization of a non-osseous structure in its spatial extent on the basis of a spatial assignment.

It goes without saying that the image data in the present connection can be stored and processed in a corresponding data-processing system, it also being possible for the representation of the image data to be chosen as desired according to the actual configuration, correspondingly by means of screens or printers or other auxiliary means.

The image data are preferably chosen to be three-dimensional, so that the entire volume of the substructure or the overall structure can be made available visually or in another suitable form—in particular also for preparation for the medical intervention. In particular, readily suitable sections and viewing angles, which can be used for preparation for the operation and for subsequently carrying it out, can be chosen from a three-dimensional image data record.

Vital structures or substructures can be readily detected and retained intraoperatively by the registration with the preoperative data, which was often not possible until now on account of inadequate orientation.

In addition, the method according to the invention makes it possible to update intraoperatively the navigation path or proposal for therapy previously determined preoperatively. This is advantageous in particular for example in the case of lesions or the like that are newly found during the operation. In this case, an operation plan prepared preoperatively on the basis of preoperative data can preferably be checked and, if appropriate, updated on the basis of the intraoperative data. This becomes possible in particular on the one hand because the circumstances found at the time during an operation, such as the position of the newly found lesion, or other information which could not be determined preoperatively, or only very inaccurately, can be integrated into the preoperatively obtained overall image and brought into a relationship with it. In addition, on the other hand, the new proposal for therapy can be detected, discussed and put into practice, both in its preoperative theoretical effects and in its intraoperative effects, directly and with minimal invasive trauma for the patient.

In a preferred way of conducting the method, a transformation can be determined between variously intraoperative image data, for example between pre- and postmutative image data or between various postmutative image data. By combination of the respective transformations, a direct relationship then follows between pre- and intraoperative image data, which can be correspondingly used for navigation.

It goes without saying that the sequences of the image data recording, the determination of the transformations and the application of the transformations are also advantageous independently of the use of a navigation aid, if the systems of coordinates necessary for the determination of a transformation can be fixed in some other way.

The position of at least one surgical implement is preferably determined during the intervention and determined in relation to the substructure or the non-osseous structure. In this way, the operating surgeon directly receives feedback on the position of his surgical implement, enabling him to use it in an extremely accurately navigated manner.

It is accordingly advantageous if the surgical instruments are sensed by suitable measuring devices and measuring points in at least five degrees of freedom, or in their main spatial degrees of freedom. In the case of axially effective instruments, such as needles or jet cutters, five degrees of freedom are normally sufficient in this respect. On the other hand, six degrees of freedom can also be sensed, allowing the corresponding or necessary transformations to be determined much more accurately.

The invention additionally proposes as a solution a navigation aid for navigation during medical interventions on non-osseous structures which has means for the definition of a local system of coordinates. Such a navigation aid, which is attached to or introduced into the non-osseous structure, already provides the operating surgeon with a purely visual or palpatory point of reference during an intervention. In addition, the local system of coordinates makes it possible to find a transformation that is applicable in the surroundings of the navigation aid, by means of which image data of these surroundings which were recorded at another point in time of the operation or in the case of a different spatial position of the non-osseous structure can then be adapted to the new position.

The invention accordingly proposes a device for navigation during medical interventions on non-osseous structures which has means for sensing the spatial position of at least one such navigation aid in at least five degrees of freedom. In this way, an automatic or computer-aided positional determination and corresponding determination of the necessary transformation can take place. Three degrees of freedom are necessary for this in order to determine the location of the navigation aid. Two further degrees of freedom are needed for the alignment of the navigation aid. If a navigation aid in the form of a needle is used and/or if a number of navigation aids are used, under some circumstances it is possible to dispense with a sixth degree of freedom, which in the case of rotational invariance of the navigation aid would not require additional fixing.

The navigation aid preferably has a marker, by which—if appropriate—the navigation aid can be sensed by an external sensor. Such a marker which can be sensed by an external sensor may be of a passive form, so that it can be particularly small and without a connection to external measuring devices or power supplies. On the other hand, such a marker may also be chosen to be active, so that it emits beams or similar information which make it detectable. The marker is preferably then provided with an energy source of its own. In this way, the in any case confined operating area is not unnecessarily constricted further by leads as a result of the navigation aid according to the invention.

Alternatively, the navigation aid may have at least one sensor for localizing at least five spatial degrees of freedom of the navigation aid. In this case, the manner in which the degrees of freedom are determined is initially of secondary importance. However, an interaction with means for generating a field, such as for example a gradient field, which permits the determination of the position and/or alignment of a sensor, has proven to be particularly advantageous. In particular, it is also possible to generate a number of gradient fields, not necessarily perpendicular to one another, so that the necessary spatial coordinates can be determined by a corresponding sensor. The corresponding measurement result can then be passed on, for example to a computer. This may take place on the one hand wirelessly but also via a corresponding data or measuring line.

In addition, the invention proposes in a preferred embodiment a navigation aid in the form of a needle or a navigation aid with a continuation in the form of a needle for navigation during medical interventions on non-osseous structures. Its needle tip can preferably define the origin of a local system of coordinates. Furthermore, the navigation aid may comprise a soft tissue anchor, which permits a translation-invariant (in the case of a navigation unit with five degrees of freedom) and additionally a rotation-invariant fixing of the navigation aid (in the case of a navigation unit with six degrees of freedom) in the non-osseous structure, and a navigation unit, which may in particular have a marker or sensor according to the invention. In the present connection, the term "navigation unit" refers to any component part of a navigation aid according to the invention which can be used or is used for localizing the navigation aid. This navigation unit permits the sensing of the navigation aid in a global system of coordinates of a tracking system, as already described above. For the same purpose, surgical instruments may also have navigation units which permit the sensing of the instruments in the coordinates of the tracking system.

The configuration of the navigation aid in the form of a needle on the one hand allows a local system of coordinates to be defined in the depth of the organ in the vicinity of the target structure, permitting depthwise navigation, and on the other hand means that only small deformations of the non-osseous structure are to be expected locally with respect to the needle if a resection is performed in its vicinity. Such an arrangement also permits more exact and simpler navigation or orientation during medical intervention, independently of the other features of the present invention.

The navigation aid preferably comprises a needle, since a needle can be introduced into such a non-osseous structure very easily and with minimal tissue lesions. In addition, depending on the indication, a needle can be inserted relatively deep into the structure, so that it can also be used directly for depthwise navigation. Depending on requirements, the navigation aid may have one or more soft tissue anchors, such as hook elements or the like, which fix the navigation aid more reliably in the structure. It goes without saying that clips or the like may also be provided in order to ensure the translation-invariant, and if appropriate also rotation-invariant, fixing of the navigation aid.

The arrangement described above is suitable in particular for interaction with a data-processing system if the navigation head or navigation aid is detectable by a tracking system. In such a case, the position of the navigation aid or of the surgical implement and also of a corresponding local system of coordinates can be readily measured, passed on to the data-processing system and its position subsequently determined with respect to the pre- and intraoperative image data.

The orientation in the area around the target structure to be operated on can in this case be achieved by a physical definition of the system of coordinates introduced in a navigated manner to the target structure by means of the navigation aids. In this system of coordinates, individual spatial points, such as for example measuring points fastened to the surgical implements or navigation units, may then be traced by suitable measuring devices for navigation. The introduced physical system of coordinates allows the global deformation of the non-osseous structure to be handled in the local system of coordinates in relation to the target structure, in which respect it goes without saying that the local system of coordinates does not necessarily have to be chosen as a Cartesian system and can possibly also be chosen to be low-dimensional. In particular, it is not necessary for the local system of coordinates also to undergo a corresponding visual or other representation in its local form. Rather, it is conceivable that it is used merely as a transformation aid and does not appear in the calculations actually to be carried out.

If a number of navigation aids are used, the deformation of relatively large regions of the non-osseous structure or of the entire non-osseous structure can be determined approximately from the registration of the positional change in relation to one another.

Further advantages, aims and properties of the present invention are explained by the following description of the accompanying drawing, in which an organ to be operated on and a corresponding surgical implement as well as a navigation aid and various systems of coordinates used are represented by way of example. In the drawing:

FIG. 1 shows a schematic representation of a liver, the first embodiment of a surgical implement according to the invention, means according to the invention for recording intraoperative image data and also a navigation aid according to the invention, FIG. 2 shows a schematic representation of a liver, a second embodiment of a surgical implement according to the invention, means according to the invention for recording intraoperative image data and also a navigation aid according to the invention, and FIG. 3 shows various systems of coordinates used in the case of the aforementioned exemplary embodiments.

Of these, FIGS. 1 and 2 show a liver 1 with a deeply located tumor 2 in the right-hand half of the liver. ("Right-hand"

refers to the liver, as considered in medicine and not to the drawings.) The right-hand liver vein 3 is completely affected by the tumor 2, while the central liver vein 4 lies a safe distance away if the tumor-bearing half of the liver is removed. The left-hand liver vein 5 is evidently not affected and has to be preserved to sustain life.

The corresponding operation is preceded by computer-aided planning for the operation, in which a three-dimensional data record of the liver is determined by means of various measuring methods, such as ultrasound, CT, MR and the like (FIG. 3, illustrations A and B). From the position of the tumor in relation to the vessels, dependent tissue and the safety margin are calculated and, from this, the resection surfaces and positions of the navigation aids are determined (compare table).

The computer-aided planning of the intervention preceding the operation generally already provides vessel structures, one or more tumors with their safety margin, calculated dependent tissue, possible cut surfaces or similar information on substructures of the non-osseous structure of interest.

After the mobilization of the liver 1, it is initially fixed intraoperatively by means of suitable anesthetic and surgical measures. These include for example jet ventilation and lining of the abdominal cavity with cloths, and fixation of the liver by means of a suitable gripping arm or by means of long needles penetrating the liver on an underlying surface.

Subsequently, in the next step, matching of the preoperatively obtained planning data with the geometry of the intraoperative site of the fixed liver 1 is performed (table). For this purpose, in the case of present exemplary embodiments, the liver 1 is scanned with three-dimensional ultrasound (FIG. 3, illustration C) and the image data record obtained in this way is registered by means of a suitable mathematical transformation with the preoperatively obtained image data, for example MR or CT image data.

At preoperatively planned locations in the vicinity of the target structure, navigation needles 6 are then introduced in a navigated manner, the sensor system 8 according to the invention for tracing the position of the navigation needles 6 being used with regard to the navigation (table A). The navigation needles 6 have a soft tissue anchor 9, by means of which the navigation needles 6 can be fixed in the liver 1 in such a way that they are secured against slipping and twisting. In the exemplary embodiment according to FIG. 1, the soft tissue anchor 9 is likewise a needle. Depending on the actual requirement for the fixing or on the system of coordinates defined by the navigation aid 6 (FIG. 3D), it is possible to dispense with this additional soft tissue anchor 9 or to make it more sophisticated, for example by hook clips or by soft tissue anchors led out from the needle tip, as presented by way of example in FIG. 2. According to a further alternative (table B), the navigation needle 6 may also be initially introduced into the liver 1 and registered in the intraoperative image data virtually together with the first recording of an intraoperative image data record.

The navigation needle 6 additionally has a navigation head, which is detectable by a tracking system. The navigation head forms a structural unit with the needle 6, with the needle tip 7, positioned near to the target structure, being regarded in the case of these exemplary embodiments as the origin of a system of coordinates (FIG. 3, illustration D). In addition, in the case of the exemplary embodiment according to FIG. 1, the needle 6 has an X-shaped cross section, so that no rotation of the needle 6 about its main axis is possible. In the case of the exemplary embodiment according to FIG. 2, this rotational invariance is ensured by the soft tissue anchor 9.

In addition, in the case of the exemplary embodiment according to FIG. 1, a tracking system is provided, which provides a corresponding sensor field for the positional determination of the navigation needles 6 (FIG. 3, illustration A). In this case, a sensor 17A—for example a camera or an IR sensor—serves the purpose of determining the position of corresponding markers 8A, 13A and 15A on the navigation needle 6 or on the navigation needles 6, on an ultrasound sensor 11 and on a jet cutter 14. In the exemplary embodiment according to FIG. 2, the tracking system comprises a magnetic gradient field 19, which is generated by two corresponding transmitters 17B and comprises two orthogonal gradient subfields, it also being possible for another sensor field to be provided cumulatively or alternatively in this respect. Optical tracking methods also come into consideration for example.

Preferably, after registration of the liver 1, at least one navigation needle 6 is used on a planned resection surface 10.

After the navigation needles 6 have been fixed, the fixing of the liver 1 can be discontinued.

The resection is carried out in the case of present exemplary embodiments by means of a jet cutter 14, which can cut by means of a water jet 16. The jet cutter 14 additionally comprises a measuring point 15A or 15B (FIG. 3, illustration E), which can be sensed by the tracking system and allows a preferably submillimeter-exact localization of the cutting implement within the spatial sensing field of the sensor 17A or within the gradient field 19 and correlation in relation to the other systems of coordinates (pre- and intraoperative image data, systems of coordinates of the navigation aids).

In addition, a Doppler ultrasound head 11 with its sensing field 12 is also fixedly connected to a measuring point 13A or 13B, which allows the positional determination of the sound plane in space and in relation to the other systems of coordinates. By means of the measurement data obtained from this (FIG. 3C), the current position of the jet cutter 14 and of the sound plane can be determined with respect to the liver 1 and its substructures.

Images from the intraoperative ultrasound can then be readily assigned to the preoperative data, because the current position and spatial relationship both of the sound plane 12 and of the navigation needle 6 are known as a result of the tracking and because the interrelationship between pre- and intraoperative image data is known as a result of the preceding registration and is preserved locally by means of the navigation needle. In this way, it is possible in particular for intraoperative and premutative image data to be determined before the actual resection during the operation and for the liver 1 and the navigation needles 6 to be registered in this way. If further lesions than those recognized during the planning are discovered in the intraoperative image data, the proposal for surgery can be modified if appropriate, in that the intraoperatively recognized lesions are transferred by coordinate transformation into the preoperative image data and the resection proposal is newly calculated in the operation planning system.

On the basis of the local systems of coordinates, set up by the 7 (FIG. 3D) navigation needles 6, the position and orientation of the entire liver 1 can be localized roughly and in its surroundings, that is in substructures such as the target structure, extremely precisely in real time. As a result, assignment of significant intraoperative structures to their preoperatively obtained models is made possible. By tracking the surgical implements 11 and 14, they can be represented in both pre- and intraoperatively obtained images in real time.

The registration of the pre- and intraoperative liver geometry with subsequent tracking of a local system of coordinates and the instruments in real time creates for the first time in soft tissue surgery the basic requirements for robotic, virtual or augmented reality. In addition, this arrangement in combination with a 3D visual presentation of the current position of the surgical implements or of the liver, including the substructures contained in it, in the pre- and intraoperative image data permits an intuitive spatial interpretation, so that, in spite of high complexity of the target structures and the absent direct sense of feel and sight with regard to the non-osseous structure itself, a good estimate of the geometrical conditions is possible.

If a further tumor is discovered by the intraoperative ultrasound 11, it is possible, as already indicated above, by means of a transformation of the intraoperative image data to the existing preoperative data for it to be readily localized, a new resection proposal prepared and then put into practice during the operation that is in progress.

It goes without saying that, apart from the liver 1, such a method can also be used in the case of other non-osseous structures.

Table:

The letters used below relate to the systems of coordinates represented in FIG. 3, whereby:

Figure 1:
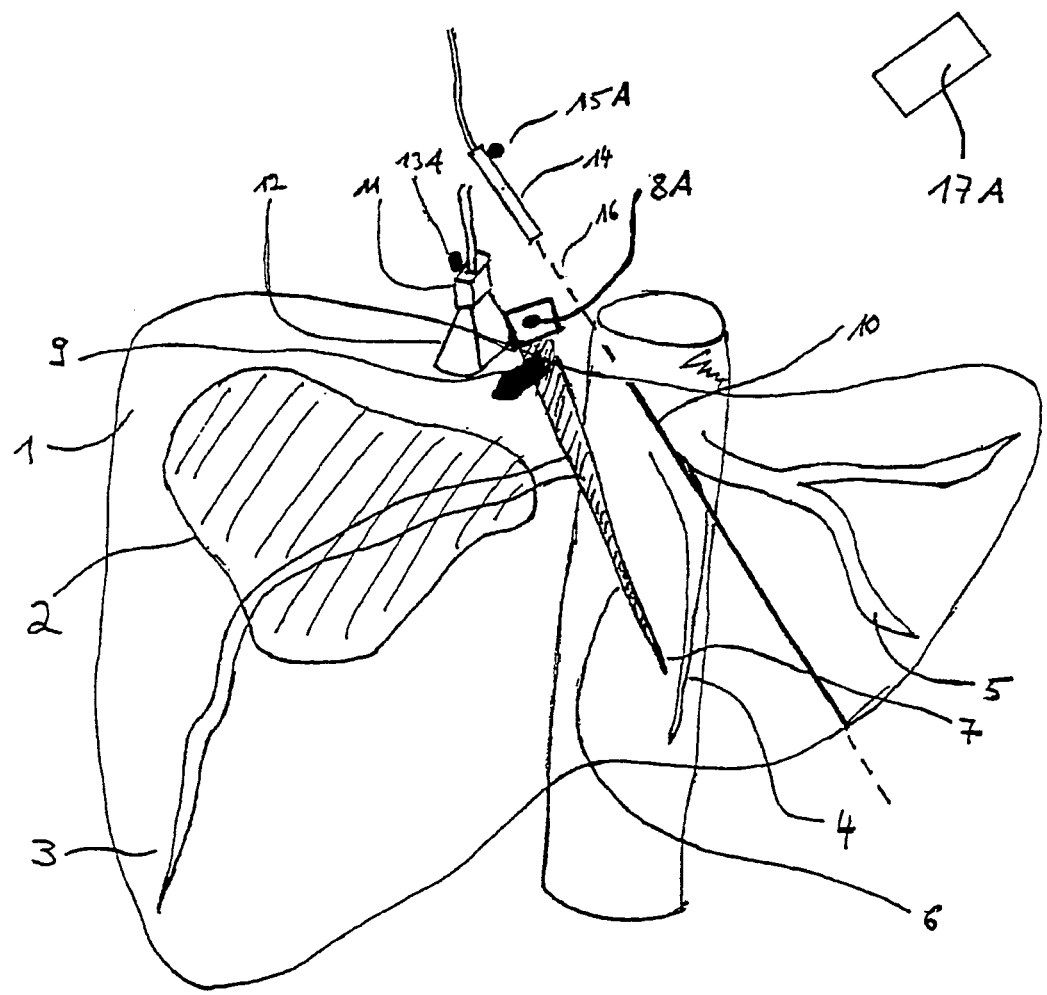
Figure 1:
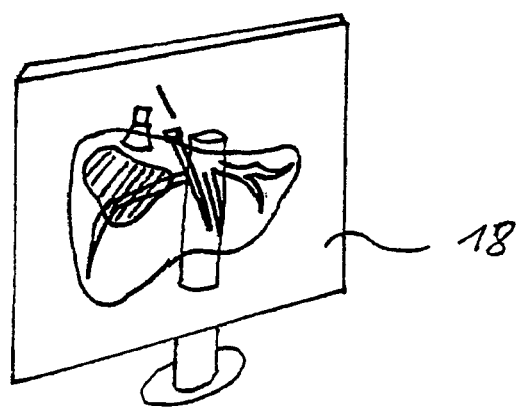
Figure 2:
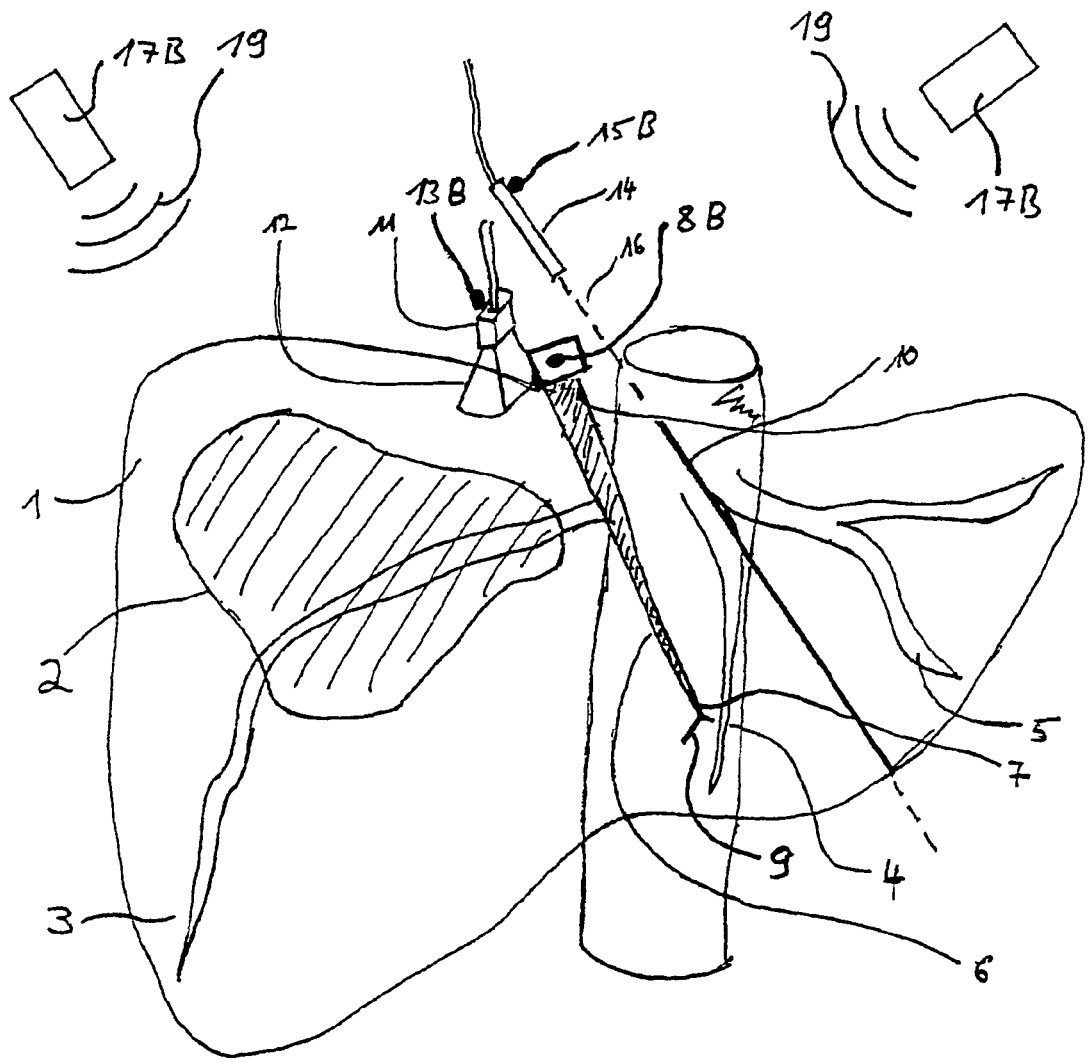
Figure 2:
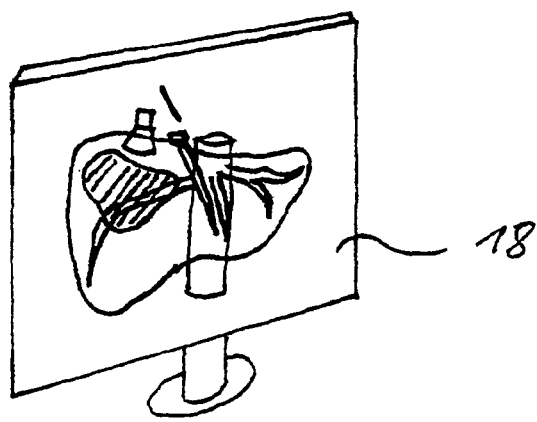
Figure 3:
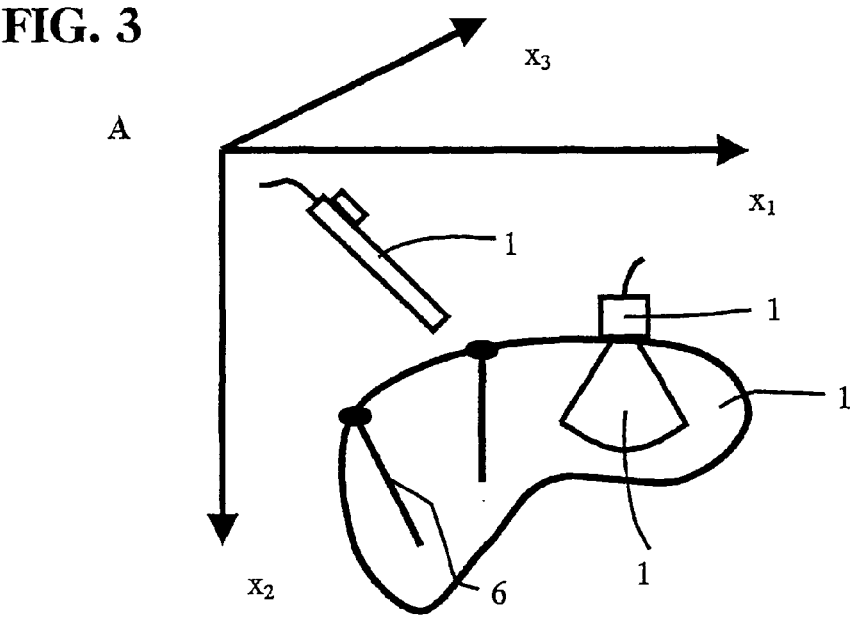
FIG. 3A shows an intraoperative global system of coordinates x.
FIG. 3B shows a system of coordinates b for preoperative data.
FIG. 3C shows an intraoperative system of coordinates u.
FIG. 3D shows a local system of cylindrical coordinates (l, r, α) which is intrahepatic or arranged within the non-osseous structure.
FIG. 3E shows a system of implement coordinates w.
Figure 3:
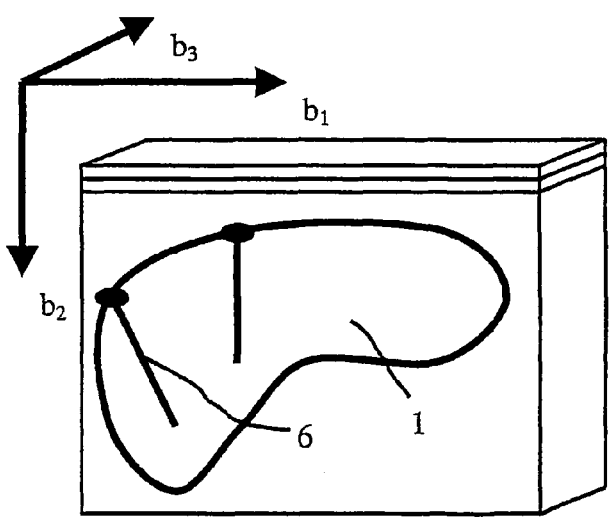
Figure 3:
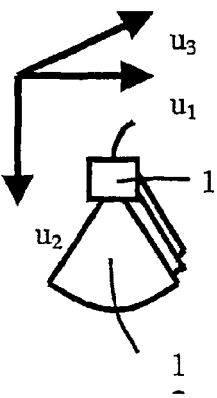
Figure 3:
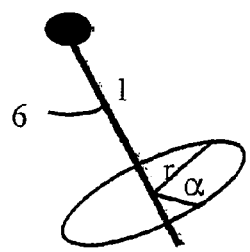
Figure 3:
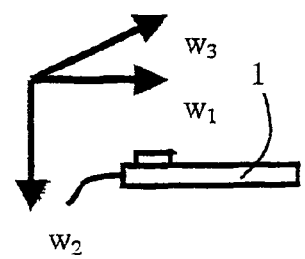

A: Navigated Setting of the Navigation Aid

| | | |
|---|---|---|
| I. | (C) → (A) → (B) | Registration of the fixed non-osseous structure. Assignment of the preoperative image data to the non-osseous structure. |
| II. | (B) → (A) → (D) | Navigated introduction of the navigation aids into the fixed non-osseous structure. Definition of local systems of coordinates. |
| III. | (E) → (A) → (D) → (B) | Assignment of a surgical instrument to the preoperative image data by means of local systems of coordinates. |
| IV. | (E) → (A) → (D) → (C) | Assignment of a surgical instrument to the intraoperative image data by means of local systems of coordinates. |
| V. | (C) → (A) → (D) → (B) | Assignment of intraoperative image data to the preoperative image data, taking into account the local systems of coordinates. |

The assignments I and II are prerequisites for the assignments III to V. After the assignment II, the fixing of the non-osseous structure can be discontinued.

B: Registration of the Navigation Aid in the Intraoperative Image Data:

| | | |
|---|---|---|
| I. | (B) → (C) → (A) → (D) | Assignment of the preoperative image data to the intraoperative image data. Extraction of the position and the orientation of the navigation aids from the intraoperative image data. |
| II. | (E) → (A) → (D) → (B) | Assignment of a surgical instrument to the preoperative image data by means of local systems of coordinates. |
| III. | (E) → (A) → (D) → (C) | Assignment of a surgical instrument to the intraoperative image data by means of local systems of coordinates. |
| IV. | (C) → (A) → (D) → (B) | Assignment of intraoperative image data to the preoperative image data, taking into account the local systems of coordinates. |

The assignments I. and II are prerequisites for the assignments III to IV.

The invention claimed is:

1. A device for navigation during a medical intervention on a non-osseous structure, comprising:
   (a) a plurality of navigation aids for navigation during a medical intervention on a non-osseous structure, each navigation aid comprising one marker defining a respective local system of coordinates for determining a position of at least one substructure of the non-osseous structure based on position of the navigation aids in the non-osseous structure, wherein each navigation aid has at least five degrees of freedom to be sensed and wherein each respective local system of coordinates of each navigation aid is locally varying; and
   (b) means for sensing the spatial position of each of the plurality of navigation aids in at least five degrees of freedom of each navigation aid.

2. The device as claimed in claim 1, comprising a plurality of navigation aids and a plurality of sensors for sensing the position of the navigation aids.

3. The device as claimed in claim 1, comprising means for localizing surgical instruments.

4. The device as claimed in claim 1, comprising a sensing field, which covers the effective radius of necessary instruments and of the navigation aids.

5. The device as claimed in claim 1, comprising means for the representation of pre- or intraoperative image data in relation to a necessary instrument.

6. The device as claimed in claim 1, comprising a plurality of navigation aids and means for generating a field, with which a sensor of each navigation aid can interact.

7. The device as claimed in claim 6, wherein the field-generating means generate at least one gradient field.

8. The device as claimed in claim 7, wherein the field-generating means generate at least two gradient fields.

9. A method for navigation during a medical intervention on a non-osseous structure comprising the steps of:
   (a) registering a non-osseous structure with preoperative data of the non-osseous structure;
   (b) fixing a plurality of navigation aids on or in the non-osseous structure in selected positions, each navigation aid comprising one marker defining a respective local system of coordinates, wherein each navigation aid has at least five degrees of freedom to be sensed;
   (c) defining the respective local system of coordinates via each navigation aid, wherein each respective local system of coordinates of each navigation aid is locally varying; and (d) determining a substructure position of at least one substructure of the non-osseous structure based on the varying positions of the navigation aids and based on the respective varying local coordinate systems.

10. The method as claimed in claim 9, wherein the non-osseous structure is registered before introduction of the navigation aids, so that the navigation aids can be attached or introduced in a navigated manner.

11. The method as claimed in claim 9, wherein a preoperative plan for the operation is prepared on the basis of the preoperative data and this plan for the operation is checked and, if appropriate, updated on the basis of the intraoperative data.

12. The method as claimed in claim 9, wherein each navigation aid further comprises a continuation in the form of a needle for introduction into the non-osseous structure.

13. The method as claimed in claim 10, wherein the non-osseous structure is immobilized or fixed prior to the registration and wherein the registration of the non-osseous structure takes place in the immobilized state, so that the navigation aids can be introduced with respect to the registered structure in a navigated manner.

14. The method as claimed in claim 13, wherein, after the attachment or introduction of the navigation aids, the immobilization or fixing of the non-osseous structure is discontinued.

15. The method as claimed in claim 9, wherein the registration of the non-osseous structure and the registration of the navigation aids take place after the introduction of the navigation aids.

16. The method as claimed in claim 15, wherein the spatial relationship of each navigation aid in relation to the non-osseous structure is determined only after introduction of the navigation aid.

17. The method as claimed in claim 9, wherein, after the registration, a transformation is determined, which assigns preoperative image data to intraoperative image data, and vice versa.

18. The method as claimed in claim 17, wherein an intraoperative transformation is determined between the intraoperative image data by means of a system of coordinates of the navigation aid, so that a direct relationship between pre- and intraoperative data is subsequently available.

* * * * *